US010246395B2

(12) United States Patent
Rogers et al.

(10) Patent No.: US 10,246,395 B2
(45) Date of Patent: Apr. 2, 2019

(54) METHODS OF ACYLATION WITH AN IONIC LIQUID CATALYZING MEDIUM

(71) Applicants: THE BOARD OF TRUSTEES OF THE UNIVERSITY OF ALABAMA, Tuscaloosa, AL (US); RELIANCE INDUSTRIES LIMITED, Navi Mumbai (IN)

(72) Inventors: Robin D. Rogers, Tuscaloosa, AL (US); Rajkumar Kore, Tuscaloosa, AL (US); Parasu Veera Uppara, Navi Mumbai (IN)

(73) Assignees: THE BOARD OF TRUSTEES OF THE UNIVERSITY OF ALABAMA, Tuscaloosa, AL (US); RELIANCE INDUSTRIES LIMITED, Navi Mumbai (IN)

( * ) Notice: Subject to any disclaimer, the term of this patent is extended or adjusted under 35 U.S.C. 154(b) by 0 days.

(21) Appl. No.: 15/846,414

(22) Filed: Dec. 19, 2017

(65) Prior Publication Data
US 2018/0170847 A1 Jun. 21, 2018

Related U.S. Application Data

(60) Provisional application No. 62/436,062, filed on Dec. 19, 2016.

(51) Int. Cl.
C07C 45/46 (2006.01)
C07C 45/00 (2006.01)

(52) U.S. Cl.
CPC .............. C07C 45/00 (2013.01); C07C 45/46 (2013.01)

(58) Field of Classification Search
CPC ..................................... C07C 45/46
See application file for complete search history.

(56) References Cited

U.S. PATENT DOCUMENTS

| 3,249,650 | A | 5/1966 | Fenske |
| 3,494,971 | A | 2/1970 | Fenske |
| 3,560,587 | A | 2/1971 | Borst, Jr. |
| 3,686,354 | A | 8/1972 | Hervert |
| 3,713,615 | A | 1/1973 | Jones |
| 4,239,931 | A | 12/1980 | Mikulicz |
| 5,824,832 | A | 10/1998 | Sherif et al. |
| 2008/0306307 | A1* | 12/2008 | Estevez Company ...... C07C 45/46 568/309 |

FOREIGN PATENT DOCUMENTS

WO 20140178075 11/2014

OTHER PUBLICATIONS

Gore, P. H. in: Olah, G.A. (Ed.), Friedel—Crafts and Related Reactions, vol. III, Wiley/Interscience, New York, 1964, p. 64.
Sheldon, R. A., Chem. Ind. 1992, 7, 903-906.
Andy et al. Acylation of 2-methoxynaphthalene and isobutylbenzene over zeolite beta. J. Catal. 2000, 192, 215-223.
Hai-Yan et al. "Effects of Chloroaluminate Ionic Liquid on Alkylation of Benzene with Mixtures of Alkenes and Alkanes." Bulletin of Catalysis Society of India, 2007, 6, 83-89.
Hegazy et al. Design, synthesis, biological evaluation, and comparative Cox1 and Cox2 docking of p-substituted benzylidenamino phenyl esters of ibuprofenic and mefenamic acids. Bioorganic and Medicinal Chemistry. 2012, 20(3), 1259.
Churakova et al. Redetermination of triethylammonium chloride in the space group P31c. Acta Crystallogr., Sect. C: Cryst. Struct. Commun. 2004, 60, 557-558.

* cited by examiner

Primary Examiner — Sikarl A Witherspoon
(74) Attorney, Agent, or Firm — Meunier Carlin & Curfman LLC

(57) ABSTRACT

Described herein are methods of acylating an aryl substrate comprising combining a substituted aryl substrate with an acylating agent in the presence of a catalyzing medium, thereby acylating the substituted aryl substrate in the para position, wherein the catalyzing medium is an ionic liquid comprising at least one cation and at least one metal halide anion.

17 Claims, 4 Drawing Sheets

METHODS OF ACYLATION WITH AN IONIC LIQUID CATALYZING MEDIUM

CROSS-REFERENCE TO RELATED APPLICATIONS

This application claims the benefit of priority to U.S. Provisional Application No. 62/436,062, filed Dec. 19, 2016, which is hereby incorporated herein by reference in its entirety.

BACKGROUND

The product, 4-isobutylacetophenone, obtained from the acylation of isobutylbenzene is largely used as an intermediate for the synthesis of ibuprofen and other pharmaceuticals. The traditional catalysts used to synthesize 4-isobutylacetophenone from the acylation of isobutylbenzene are $AlCl_3$, hydrofluoric acid (HF), and zeolites. $AlCl_3$ is used in higher than stoichiometric amounts, results in large amounts of waste, and is non-regenerable after the reaction (U.S. Pat. No. 3,385,886; Gore P H. in: Olah G A. (Ed.), Friedel-Crafts and Related Reactions, vol. III, Wiley/Interscience, New York, 1964, p. 64). HF is an extremely toxic, volatile, and corrosive chemical, and is typically used in higher than stoichiometric amounts relative to isobutylbenzene for this reaction (Sheldon R A. *Chem. Ind.* 1992, 7, 903-906). Zeolites result in low product yield (e.g., <6%) (Andy P. *J. Catal.* 2000, 192, 215-223). Based on these limitations of existing catalysts, new catalysts and/or catalyzing mediums for the acylation of isobutylbenzene and similar functionalized aryl compounds are needed. The methods discuss herein address these and other needs.

SUMMARY

In accordance with the purposes of the disclosed systems and methods, as embodied and broadly described herein, the disclosed subject matter relates to methods for acylation using an ionic liquid catalyzing medium.

Additional advantages of the disclosed systems and methods will be set forth in part in the description which follows, and in part will be obvious from the description. The advantages of the disclosed systems and methods will be realized and attained by means of the elements and combinations particularly pointed out in the appended claims. It is to be understood that both the foregoing general description and the following detailed description are exemplary and explanatory only and are not restrictive of the disclosed systems and methods, as claimed.

The details of one or more embodiments of the invention are set forth in the accompanying drawings and the description below. Other features, objects, and advantages of the invention will be apparent from the description and drawings, and from the claims.

BRIEF DESCRIPTION OF THE FIGURES

The accompanying figures, which are hereby incorporated in and constitute a part of this specification, illustrate several aspects of the disclosure, and together with the description, serve to explain the principles of the disclosure.

DETAILED DESCRIPTION

Figure 1:
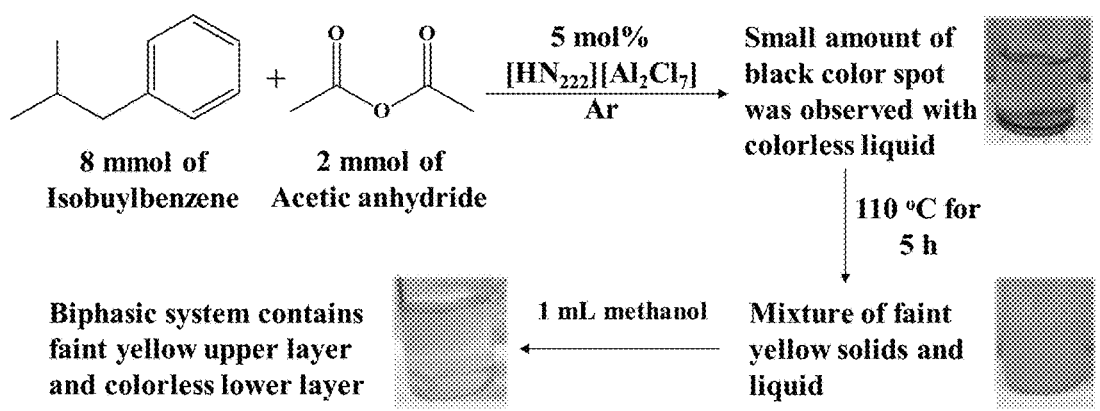
FIG. 1 is a schematic of the acylation of isobutylbenzene reaction using a chloroaluminate ionic liquid.

The materials, compositions, articles, and methods described herein can be understood more readily by reference to the following detailed description of specific aspects of the disclosed subject matter and the Examples included therein.

Before the present materials, compositions, articles, devices, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings:

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "an ionic liquid" includes mixtures of two or more such ionic liquids, reference to "the compound" includes mixtures of two or more such compounds, and the like.

"Optional" or "optionally" means that the subsequently described event or circumstance can or cannot occur, and that the description includes instances where the event or circumstance occurs and instances where it does not.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed, then "less than or equal to" the value, "greater than or equal to the value," and possible ranges between values are also disclosed, as appropriately understood by the skilled artisan. For example, if the value "10" is disclosed, then "less than or equal to 10" as well as "greater than or equal to 10" is also disclosed. It is also understood that throughout the application data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Chemical Definitions

Terms used herein will have their customary meaning in the art unless specified otherwise. The organic moieties mentioned when defining variable positions within the general formulae described herein (e.g., the term "halogen") are collective terms for the individual substituents encompassed by the organic moiety. The prefix $C_n$-$C_m$ preceding a group or moiety indicates, in each case, the possible number of carbon atoms in the group or moiety that follows.

References in the specification and concluding claims to the molar ratio of a particular element or component in a composition denotes the molar relationship between the element or component and any other elements or components in the composition or article for which a part by weight is expressed. Thus, in a compound containing 2 moles of X and 5 moles of Y, X and Y are present at a molar ratio of 2:5, and are present in such ratio regardless of whether additional components are contained in the compound.

A weight percent (wt. %) of a component, unless specifically stated to the contrary, is based on the total weight of the formulation or composition in which the component is included.

The term "ion," as used herein, refers to any molecule, portion of a molecule, cluster of molecules, molecular complex, moiety, or atom that contains a charge (positive, negative, or both at the same time within one molecule, cluster of molecules, molecular complex, or moiety (e.g., zwitterions)) or that can be made to contain a charge. Methods for producing a charge in a molecule, portion of a molecule, cluster of molecules, molecular complex, moiety, or atom are disclosed herein and can be accomplished by methods known in the art, e.g., protonation, deprotonation, oxidation, reduction, alkylation, acetylation, esterification, deesterification, hydrolysis, etc.

The term "anion" is a type of ion and is included within the meaning of the term "ion." An "anion" is any molecule, portion of a molecule (e.g., zwitterion), cluster of molecules, molecular complex, moiety, or atom that contains a net negative charge or that can be made to contain a net negative charge. The term "anion precursor" is used herein to specifically refer to a molecule that can be converted to an anion via a chemical reaction (e.g., deprotonation).

The term "cation" is a type of ion and is included within the meaning of the term "ion." A "cation" is any molecule, portion of a molecule (e.g., zwitterion), cluster of molecules, molecular complex, moiety, or atom, that contains a net positive charge or that can be made to contain a net positive charge. The term "cation precursor" is used herein to specifically refer to a molecule that can be converted to a cation via a chemical reaction (e.g., protonation or alkylation).

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, heteroatoms present in a compound or moiety, such as nitrogen, can have hydrogen substituents and/or any permissible substituents of organic compounds described herein which satisfy the valency of the heteroatom. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound (e.g., a compound that does not spontaneously undergo transformation such as by rearrangement, cyclization, elimination, etc.

"$Z^1$," "$Z^2$," "$Z^3$," and "$Z^4$" are used herein as generic symbols to represent various specific substituents. These symbols can be any substituent, not limited to those disclosed herein, and when they are defined to be certain substituents in one instance, they can, in another instance, be defined as some other substituents.

As used herein, the term "alkyl" refers to saturated, straight-chained or branched saturated hydrocarbon moieties. Unless otherwise specified, $C_1$-$C_{50}$ (e.g., $C_1$-$C_{45}$, $C_1$-$C_{40}$, $C_1$-$C_{35}$, $C_1$-$C_{30}$, $C_1$-$C_{25}$, $C_1$-$C_{20}$, $C_1$-$C_{18}$, $C_1$-$C_{16}$, $C_1$-$C_{14}$, $C_1$-$C_{12}$, $C_1$-$C_{10}$, $C_1$-$C_8$, $C_1$-$C_6$, or $C_1$-$C_4$) alkyl groups are intended. Examples of alkyl groups include methyl, ethyl, propyl, 1-methyl-ethyl, butyl, 1-methyl-propyl, 2-methyl-propyl, 1,1-dimethyl-ethyl, pentyl, 1-methyl-butyl, 2-methyl-butyl, 3-methyl-butyl, 2,2-dimethyl-propyl, 1-ethyl-propyl, hexyl, 1,1-dimethyl-propyl, 1,2-dimethyl-propyl, 1-methyl-pentyl, 2-methyl-pentyl, 3-methyl-pentyl, 4-methyl-pentyl, 1,1-dimethyl-butyl, 1,2-dimethyl-butyl, 1,3-dimethyl-butyl, 2,2-dimethyl-butyl, 2,3-dimethyl-butyl, 3,3-dimethyl-butyl, 1-ethyl-butyl, 2-ethyl-butyl, 1,1,2-trimethyl-propyl, 1,2,2-trimethyl-propyl, 1-ethyl-1-methyl-propyl, and 1-ethyl-2-methyl-propyl. Alkyl substituents may be unsubstituted or substituted with one or more chemical moieties. The alkyl group can be substituted with one or more groups including, but not limited to, hydroxy, halogen, acyl, alkyl, alkoxy, alkenyl, alkynyl, aryl, heteroaryl, aldehyde, amino, cyano, carboxylic acid, ester, ether, ketone, nitro, phosphonyl, silyl, sulfo-oxo, sulfonyl, sulfone, sulfoxide, or thiol, as described below, provided that the substituents are sterically compatible and the rules of chemical bonding and strain energy are satisfied.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halides (halogens; e.g., fluorine, chlorine, bromine, or iodine). The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

As used herein, the term "alkenyl" refers to unsaturated, straight-chained, or branched hydrocarbon moieties containing a double bond. Unless otherwise specified, $C_2$-$C_{50}$ (e.g., $C_2$-$C_{45}$, $C_2$-$C_{40}$, $C_2$-$C_{35}$, $C_2$-$C_{30}$, $C_2$-$C_{25}$, $C_2$-$C_{20}$, $C_2$-$C_{18}$, $C_2$-$C_{16}$, $C_2$-$C_{14}$, $C_2$-$C_{12}$, $C_2$-$C_{10}$, $C_2$-$C_8$, $C_2$-$C_6$, or $C_2$-$C_4$) alkenyl groups are intended. Alkenyl groups may contain more than one unsaturated bond. Examples include ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, and 1-ethyl-2-methyl-2-propenyl. The term "vinyl" refers to a group having the structure —CH=CH$_2$; 1-propenyl refers to a group with the structure -CH=CH—CH$_3$; and 2-propenyl refers to a group with the structure —CH$_2$—CH=CH$_2$. Asymmetric structures such as $(Z^1Z^2)C=C(Z^3Z^4)$ are intended to include both the E and Z isomers. This can be presumed in structural formulae herein wherein an asymmetric alkene is present, or it can be explicitly indicated by the bond symbol C=C. Alkenyl substituents may be unsubstituted or substituted with one or more chemical moieties. Examples of suitable substituents include, for example, alkyl, halogenated alkyl, alkoxy, alkenyl, alkynyl, aryl, heteroaryl, acyl, aldehyde, amino, cyano, carboxylic acid, ester, ether, halide, hydroxy, ketone, nitro, phosphonyl, silyl, sulfo-oxo, sulfonyl, sulfone, sulfoxide, or thiol, as described below, provided that the substituents are sterically compatible and the rules of chemical bonding and strain energy are satisfied.

As used herein, the term "alkynyl" represents straight-chained or branched hydrocarbon moieties containing a triple bond. Unless otherwise specified, $C_2$-$C_{50}$ (e.g., $C_2$-$C_{45}$, $C_2$-$C_{40}$, $C_2$-$C_{35}$, $C_2$-$C_{30}$, $C_2$-$C_{25}$, $C_2$-$C_{20}$, $C_2$-$C_{18}$, $C_2$-$C_{16}$, $C_2$-$C_{14}$, $C_2$-$C_{12}$, $C_2$-$C_{10}$, $C_2$-$C_8$, $C_2$-$C_6$, or $C_2$-$C_4$) alkynyl groups are intended. Alkynyl groups may contain more than one unsaturated bond. Examples include $C_2$-$C_6$-alkynyl, such as ethynyl, 1-propynyl, 2-propynyl (or propargyl), 1-butynyl, 2-butynyl, 3-butynyl, 1-methyl-2-propynyl, 1-pentynyl, 2-pentynyl, 3-pentynyl, 4-pentynyl, 3-methyl-1-butynyl, 1-methyl-2-butynyl, 1-methyl-3-butynyl, 2-methyl-3-butynyl, 1,1-dimethyl-2-propynyl, 1-ethyl-2-propynyl, 1-hexynyl, 2-hexynyl, 3-hexynyl, 4-hexynyl, 5-hexynyl, 3-methyl-1-pentynyl, 4-methyl-1-pentynyl, 1-methyl-2-pentynyl, 4-methyl-2-pentynyl, 1-methyl-3-pentynyl, 2-methyl-3-pentynyl, 1-methyl-4-pentynyl, 2-methyl-4-pentynyl, 3-methyl-4-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl, and 1-ethyl-1-methyl-2-propynyl. Alkynyl substituents may be unsubstituted or substituted with one or more chemical moieties. Examples of suitable substituents include, for example, alkyl, halogenated alkyl, alkoxy, alkenyl, alkynyl, aryl, heteroaryl, acyl, aldehyde, amino, cyano, carboxylic acid, ester, ether, halide, hydroxy, ketone, nitro, phosphonyl, silyl, sulfo-oxo, sulfonyl, sulfone, sulfoxide, or thiol, as described below.

As used herein, the term "aryl," as well as derivative terms such as aryloxy, refers to groups that include a monovalent aromatic carbocyclic group of from 3 to 50 carbon atoms. Aryl groups can include a single ring or multiple condensed rings. In some embodiments, aryl groups include $C_6$-$C_{10}$ aryl groups. Examples of aryl groups include, but are not limited to, phenyl, biphenyl, naphthyl, tetrahydronaphtyl, phenylcyclopropyl, and indanyl. In some embodiments, the aryl group can be a phenyl, indanyl or naphthyl group. The term "heteroaryl" is defined as a group that contains an aromatic group that has at least one heteroatom incorporated within the ring of the aromatic group. Examples of heteroatoms include, but are not limited to, nitrogen, oxygen, sulfur, and phosphorus. The term "non-heteroaryl," which is included in the term "aryl," defines a group that contains an aromatic group that does not contain a heteroatom. The aryl or heteroaryl substituents may be unsubstituted or substituted with one or more chemical moieties. Examples of suitable substituents include, for example, alkyl, halogenated alkyl, alkoxy, alkenyl, alkynyl, aryl, heteroaryl, acyl, aldehyde, amino, cyano, carboxylic acid, ester, ether, halide, hydroxy, ketone, nitro, phosphonyl, silyl, sulfo-oxo, sulfonyl, sulfone, sulfoxide, or thiol as described herein. The term "biaryl" is a specific type of aryl group and is included in the definition of aryl. Biaryl refers to two aryl groups that are bound together via a fused ring structure, as in naphthalene, or are attached via one or more carbon-carbon bonds, as in biphenyl.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl" is a cycloalkyl group as defined above where at least one of the carbon atoms of the ring is substituted with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, alkoxy, alkenyl, alkynyl, aryl, heteroaryl, acyl, aldehyde, amino, cyano, carboxylic acid, ester, ether, halide, hydroxy, ketone, nitro, phosphonyl, silyl, sulfo-oxo, sulfonyl, sulfone, sulfoxide, or thiol as described herein.

The term "cycloalkenyl" as used herein is a non-aromatic carbon-based ring composed of at least three carbon atoms and containing at least one double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, and the like. The term "heterocycloalkenyl" is a type of cycloalkenyl group as defined above, and is included within the meaning of the term "cycloalkenyl," where at least one of the carbon atoms of the ring is substituted with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, alkoxy, alkenyl, alkynyl, aryl, heteroaryl, acyl, aldehyde, amino, cyano, carboxylic acid, ester, ether, halide, hydroxy, ketone, nitro, phosphonyl, silyl, sulfo-oxo, sulfonyl, sulfone, sulfoxide, or thiol as described herein.

The term "cyclic group" is used herein to refer to either aryl groups, non-aryl groups (i.e., cycloalkyl, heterocycloalkyl, cycloalkenyl, and heterocycloalkenyl groups), or both. Cyclic groups have one or more ring systems that can be substituted or unsubstituted. A cyclic group can contain one or more aryl groups, one or more non-aryl groups, or one or more aryl groups and one or more non-aryl groups.

The term "acyl" as used herein is represented by the formula —C(O)$Z^1$ where $Z^1$ can be a hydrogen, hydroxyl, alkoxy, alkyl, halogenated alkyl, alkenyl, alkynyl, aryl, heteroaryl, cycloalkyl, cycloalkenyl, heterocycloalkyl, or heterocycloalkenyl group described above. As used herein, the term "acyl" can be used interchangeably with "carbonyl." Throughout this specification "C(O)" or "CO" is a short hand notation for C=O.

As used herein, the term "alkoxy" refers to a group of the formula $Z^1$—O—, where $Z^1$ is unsubstituted or substituted alkyl as defined above. Unless otherwise specified, alkoxy groups wherein $Z^1$ is a $C_1$-$C_{50}$ (e.g., $C_1$-$C_{45}$, $C_1$-$C_{40}$, $C_1$-$C_{35}$, $C_1$-$C_{30}$, $C_1$-$C_{25}$, $C_1$-$C_{20}$, $C_1$-$C_{18}$, $C_1$-$C_{16}$, $C_1$-$C_{14}$, $C_1$-$C_{12}$, $C_1$-$C_{10}$, $C_1$-$C_8$, $C_1$-$C_6$, $C_1$-$C_4$) alkyl group are intended. Examples include methoxy, ethoxy, propoxy, 1-methyl-ethoxy, butoxy, 1-methyl-propoxy, 2-methyl-propoxy, 1,1-dimethyl-ethoxy, pentoxy, 1-methyl-butyloxy, 2-methyl-butoxy, 3-methyl-butoxy, 2,2-di-methyl-propoxy, 1-ethyl-propoxy, hexoxy, 1,1-dimethyl-propoxy, 1,2-dimethyl-propoxy, 1-methyl-pentoxy, 2-methyl-pentoxy, 3-methyl-pentoxy, 4-methyl-pentoxy, 1,1-dimethyl-butoxy, 1,2-dimethyl-butoxy, 1,3-dimethyl-butoxy, 2,2-dimethyl-butoxy, 2,3-dimethyl-butoxy, 3,3-dimethyl-butoxy, 1-ethyl-butoxy, 2-ethylbutoxy, 1,1,2-trimethyl-propoxy, 1,2,2-trimethyl-propoxy, 1-ethyl-1-methyl-propoxy, and 1-ethyl-2-methyl-propoxy.

The term "aldehyde" as used herein is represented by the formula —C(O)H.

The terms "amine" or "amino" as used herein are represented by the formula —N$Z^1Z^2$, where $Z^1$ and $Z^2$ can each be substitution group as described herein, such as hydrogen, an alkyl, halogenated alkyl, alkenyl, alkynyl, aryl, heteroaryl, cycloalkyl, cycloalkenyl, heterocycloalkyl, or heterocycloalkenyl group described above. "Amido" is —C(O)N$Z^1Z^2$.

The term "carboxylic acid" as used herein is represented by the formula —C(O)OH. A "carboxylate" or "carboxyl" group as used herein is represented by the formula —C(O)O$^-$.

The term "cyano" as used herein is represented by the formula —CN.

The term "ester" as used herein is represented by the formula —OC(O)$Z^1$ or —C(O)O$Z^1$, where $Z^1$ can be an alkyl, halogenated alkyl, alkenyl, alkynyl, aryl, heteroaryl, cycloalkyl, cycloalkenyl, heterocycloalkyl, or heterocycloalkenyl group described above.

The term "ether" as used herein is represented by the formula $Z^1$O$Z^2$, where $Z^1$ and $Z^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "ketone" as used herein is represented by the formula $Z^1$C(O)$Z^2$, where $Z^1$ and $Z^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "halide" or "halogen" or "halo" as used herein refers to fluorine, chlorine, bromine, and iodine.

The term "hydroxyl" as used herein is represented by the formula —OH.

The term "nitro" as used herein is represented by the formula —NO$_2$.

The term "phosphonyl" is used herein to refer to the phospho-oxo group represented by the formula —P(O)(O$Z^1$)$_2$, where $Z^1$ can be hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "silyl" as used herein is represented by the formula —Si$Z^1Z^2Z^3$, where $Z^1$, $Z^2$, and $Z^3$ can be, independently, hydrogen, alkyl, halogenated alkyl, alkoxy, alkenyl, alkynyl, aryl, heteroaryl, cycloalkyl, cycloalkenyl, heterocycloalkyl, or heterocycloalkenyl group described above.

The term "sulfonyl" is used herein to refer to the sulfooxo group represented by the formula —S(O)$_2Z^1$, where $Z^1$ can be hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "sulfonylamino" or "sulfonamide" as used herein is represented by the formula —S(O)$_2$NH—.

The term "thiol" as used herein is represented by the formula —SH.

The term "sulfide" as used herein is comprises the formula —S—.

As used herein, Me refers to a methyl group; OMe refers to a methoxy group; and i-Pr refers to an isopropyl group.

"$R^1$," "$R^2$," "$R^3$," "$R^n$," etc., where n is some integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an amine group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

Unless stated to the contrary, a formula with chemical bonds shown only as solid lines and not as wedges or dashed lines contemplates each possible stereoisomer or mixture of stereoisomer (e.g., each enantiomer, each diastereomer, each meso compound, a racemic mixture, or scalemic mixture).

Reference will now be made in detail to specific aspects of the disclosed materials, compounds, compositions, articles, and methods, examples of which are illustrated in the accompanying Examples and Figures.

Methods of Acylation

Described herein are methods of acylating an aryl substrate comprising combining a substituted aryl substrate with an acylating agent in the presence of a catalyzing medium, thereby acylating the substituted aryl substrate in the para position. The catalyzing medium comprises an ionic liquid. In some examples, the ionic liquid comprises at least one cation and at least one metal halide anion, as described herein.

The term "ionic liquid" has many definitions in the art, but is used herein to refer to salts (i.e., compositions comprising cations and anions) that are liquid at a temperature of at or below about 150° C., e.g., at or below about 120, 100, 80, 60, 40, or 25° C. That is, at one or more temperature ranges or points at or below about 150° C. the disclosed ionic liquid compositions are liquid; although, it is understood that they can be solids at other temperature ranges or points. An ionic liquid is not considered a mere solution containing ions as solutes dissolved therein.

The use of the term "liquid" to describe the disclosed ionic liquid compositions is meant to describe a generally amorphous, non-crystalline, or semi-crystalline state. For example, while some structured association and packing of cations and anions can occur at the atomic level, the disclosed ionic liquid compositions have minor amounts of such ordered structures and are therefore not crystalline solids. The compositions disclosed herein can be fluid and free-flowing liquids or amorphous solids such as glasses or waxes at a temperature at or below about 150° C. In particular examples disclosed herein, the disclosed ionic liquid compositions are liquid at which the composition is applied (i.e., ambient temperature).

Further, the disclosed ionic liquid compositions are materials composed of at least two different ions; each of which can independently and simultaneously introduce a specific characteristic to the composition not easily obtainable with traditional dissolution and formulation techniques. Thus, by providing different ions and ion combinations, one can change the characteristics or properties of the disclosed ionic liquid compositions in a way not seen by simply preparing various crystalline salt forms. Examples of characteristics that can be controlled in the disclosed compositions include, but are not limited to, melting, solubility control, and rate of dissolution. It is this multi-nature/functionality of the disclosed ionic liquid compositions which allows one to fine-tune or design in very specific desired material properties.

The ionic liquids disclosed herein can be used in the disclosed methods neat; that is, there are no or substantially no (e.g., less than 5 or less than 1 mole %) solvents or other materials besides the aryl substrate and acylating agent present in the reaction. For example, the disclosed methods can be solvent less or substantially solventless wherein there is no solvent or other materials in the reaction besides the reactants and ionic liquid.

As disclosed herein, the ionic liquids can include at least one metal halide anion. In some embodiments, the disclosed ionic liquids can include two or more anions (e.g., 3, 4, 5, 6, 7, 8, 9, 10, or more anions). The anions in the disclosed ionic liquids can be the same or different. In some aspects, the anions in the disclosed ionic liquids can be different, that is, the ionic liquids can comprise more than one kind of anion (e.g., 2, 3, 4, 5, 6, 7, 8, 9, 10, or more different kinds of anions).

The anions in the disclosed ionic liquids can each be independently selected from metal halide anions (also referred to herein as "halometallates"). The term "metal halide anion" as used herein refers to a complex polyatomic anion, which contain at least a halogen bonded to a primary metal. These complexes may have a number of halogen atoms bonded to the primary metal in excess of the usual valence number of the metal. Alternatively, one or more of such halogen can be replaced by oxygen or other atoms. The term "primary metal" is used to refer to a metal that can form a complex anion with a halogen. In some embodiments, the ionic liquid can include at least two metal halide anions.

In some embodiments, the primary metal in the metal halide anions can include a metal selected from Group II or Group III of the periodic table, transition metals, or combinations thereof. In some examples, the primary metal can be selected from aluminum, iron, chromium, zinc, copper, tin, titanium, palladium, zirconium, gallium, and combinations thereof. In some examples the at least one metal halide anion comprises an aluminum halide.

The metal halide anions disclosed herein can include at least one halide selected from Cl, F, Br, and I. In some examples, the at least one metal halide anion comprises a metal chloride.

In some examples, the at least one metal halide anion in the ionic liquids disclosed herein can be selected from chloroaluminate, chlorozincate, chloroferrate, chlorogallate, chlorostannate, chloroindate, chlorochromate, chlorocuprate, chlorotitannate, chlorozirconate, chloropalladate, and combinations thereof. In some examples, the at least one metal halide anion can comprise chloroaluminate. In some examples, the at least one metal halide anion can comprise $[Al_2Cl_7]^-$.

The at least two metal halide anions can be incorporated into the ionic liquids in any suitable molar ratio so long as there is a balance of charge with the cation(s). As disclosed herein, the ionic liquids can include at least one cation. For example, the disclosed ionic liquids can comprise one or more cations (e.g., 2, 3, 4, 5, 6, 7, 8, 9, 10, or more different cations). The cations in the disclosed ionic liquids can be the same or different. In some aspects, the cations in the disclosed ionic liquids can be different, that is, the ionic liquids can comprise more than one kind of cation (e.g., 2, 3, 4, 5, 6, 7, 8, 9, 10, or more different kinds of cations).

The cation in the disclosed ionic liquids can be an organic group-containing cation (also referred to herein as "organic cation"). The organic cation can be a complex polyatomic cation, which contains at least an organic group bonded to a heteroatom. In some embodiments, the ionic liquid can include at least one organic cation.

Particular examples of organic cations that can be present in the disclosed ionic liquids include compounds that contain one or more heteroatoms (e.g., nitrogen, phosphorus, oxygen, or sulfur heteroatom(s)). For example, the organic cation can comprise a linear, branched, or cyclic compound comprising one or more heteroatoms.

Nitrogen atom-containing groups can exist as a neutral compound or can be converted to a positively-charged quaternary ammonium species, for example, through alkylation or protonation of the nitrogen atom. Thus, compounds that possess a quaternary nitrogen atom (known as quaternary ammonium compounds (QACs)) are typically cations. According to the methods and compositions disclosed herein, any compound that contains a quaternary nitrogen atom or a nitrogen atom that can be converted into a quaternary nitrogen atom (cation precursor) can be a suitable cation for the disclosed ionic liquids.

In some examples, phosphorous atoms can exist as a charged phosphonium species, for example, through alkylation of the phosphorous atom. Thus, compounds that possess a quaternary phosphorous atom (known as quaternary phosphonium compounds) are typically cations. According to the methods and compositions disclosed herein, any compound that contains a quaternary phosphorus atom or a phosphorus atom that can be converted into a quaternary phosphonium atom can be a suitable cation for the disclosed ionic liquids.

In some examples, sulfur atoms can exist as a charged sulfonium species, for example, through alkylation of the sulfurous atom. Thus, compounds that possess a ternary sulfurous atom are typically cations. According to the methods and compositions disclosed herein, any compound that contains a ternary sulfurous atom or a sulfurous atom that can be converted into a ternary sulfurous atom can be a suitable cation for the disclosed ionic liquids.

Some specific organic cations suitable for use herein are heteroaryls. In some embodiments, the heteroaryl can be an aliphatic heteroaryl. An aliphatic heteroaryl cation is a compound that comprises at least one aliphatic moiety bonded to a heteroaryl moiety. In the aliphatic heteroaryl cation, the aliphatic moiety can be any alkyl, alkenyl, alkynyl, heteroalkyl, heteroalkenyl, heteroalkynyl, cycloalkyl, cycloalkenyl, heterocycloalkyl, or heterocycloalkenyl group, as described herein.

In the heteroaryl cation, the heteroaryl moiety can be any heteroaryl moiety as described herein. For example, the heteroaryl moiety can be an aryl group having a nitrogen atom and optionally one or more heteroatoms (e.g., oxygen, sulfur, phosphorous, or halonium). Examples of specific heteroaryl moieties that can be used in the heteroaryl cations include, but are not limited to, substituted or unsubstituted benztriazoliums, substituted or unsubstituted benzimidazoliums, substituted or unsubstituted benzothiazoliums, substituted or unsubstituted pyridiniums, substituted or unsubstituted pyridaziniums, substituted or unsubstituted pyrimidiniums, substituted or unsubstituted pyraziniums, substituted or unsubstituted imidazoliums, substituted or unsubstituted pyrazoliums, substituted or unsubstituted oxazoliums, substituted or unsubstituted 1,2,3-triazoliums, substituted or unsubstituted 1,2,4-triazoliums, substituted or unsubstituted thiazoliums, substituted or unsubstituted piperidiniums, substituted or unsubstituted pyrrolidiniums, substituted or unsubstituted quinoliums, and substituted or unsubstituted isoquinoliums. As described herein, when the heteroatom of the heteroaryl is nitrogen, this forms a quaternary ammonium cation.

Some specific organic cations suitable for use herein are cyclic compounds comprising one or more heteroatoms. For example, the organic cation can comprise a pyridinyl moiety, imidazolinyl moiety, or the like that can have substituted or unsubstituted linear or branched alkyl units attached thereto. In some examples, the organic cation can comprise a single heteroatom wherein a sufficient number of substituted or unsubstituted linear or branched alkyl units are attached to the heteroatom such that a cation is formed. For example, the organic cation can comprise $C_n$ alkylmethylimidazolium [$C_n$mim] where n is an integer of from 1 to 8. Preferably, the cation $C_1$-4 alkyl-methylimidazolium [$C_{1-4}$mim] can be used. Other non-limiting examples of heterocyclic and heteroaryl units that can be alkylated to form cationic units include substituted or unsubstituted furans, substituted or unsubstituted benzofurans, substituted or unsubstituted dibenzofurans, substituted or unsubstituted indolizines, substituted or unsubstituted isoindoles, substituted or unsubstituted indoles, substituted or unsubstituted indolines, substituted or unsubstituted indazoles, substituted or unsubstituted imidazoles, substituted or unsubstituted morpholiniums, substituted or unsubstituted morpholines, substituted or unsubstituted oxazoles, substituted or unsubstituted oxaphospholes, substituted or unsubstituted oxothiazoles, substituted or unsubstituted oxazines, substituted or unsubstituted oxazolines, substituted or unsubstituted phenazine, substituted or unsubstituted phthalazines, substituted or unsubstituted purines, substituted or unsubstituted pyrroles, substituted or unsubstituted pyrazoles, substituted or unsubstituted pyridines, substituted or unsubstituted pyrazines, substituted or unsubstituted pyrimidines, substituted or unsubstituted pryidazines, substituted or unsubstituted phospholes, substituted or unsubstituted pentazoles, substituted or unsubstituted pyridazines, substituted or unsubstituted piperazines, substituted or unsubstituted piperidines, substituted or unsubstituted pyrans, substituted or unsubstituted isoquinolines, substituted or unsubstituted quinolines, substituted or unsubstituted quinoxalines, substituted or unsubstituted quinazolines, substituted or unsubstituted selenozoles, substituted or unsubstituted triazoles, substituted or unsubstituted thiazoles, substituted or unsubstituted isothiazoles, substituted or unsubstituted dithiazoles, substituted or unsubstituted azathiazoles, substituted or unsubstituted thiophenes, substituted or unsubstituted benzothiophenes, substituted or unsubstituted dibenzothiophenes, substituted or unsubstituted tetrazoles, substituted or unsubstituted thiadiazoles, and the like, including derivatives and mixtures thereof.

In some examples, the disclosed ionic liquid compositions can comprise an ammonium cation of the structure $NR^1R^2R^3R^4$, wherein $R^1$, $R^2$, $R^3$, and $R^4$ are independently H, halogen, substituted or unsubstituted $C_1$-$C_{20}$ alkyl, substituted or unsubstituted $C_1$-$C_8$ cycloalkyl, or wherein, as valence permits, two or more of $R^1$, $R^2$, $R^3$, and $R^4$, together with the atoms to which they are attached, form a 3-10 membered cyclic moiety. In some examples, the disclosed anionic liquid compositions can comprise an aniline cation.

In some examples, $R^1$, $R^2$, $R^3$, and $R^4$ are independently H or substituted or unsubstituted $C_1$-$C_8$ alkyl. In some examples, $R^1$, $R^2$, $R^3$, and $R^4$ are independently H or unsubstituted $C_1$-$C_8$ alkyl. In some examples, $R^1$, $R^2$, $R^3$, and $R^4$ are independently H or unsubstituted $C_1$-$C_4$ alkyl. In some examples, $R^1$ is H. In some examples, $R^2$, $R^3$ and $R^4$ are $C_2H_5$. In some examples, the at least one ammonium cation comprises $[HN(C_2H_5)_3]^+$.

In some examples, the ionic liquid catalyzing medium can comprise $[HN_{222}][Al_2Cl_7]$, where the notation "$HN_{222}$" indicates a triethylammonium group.

In some examples, the disclosed ionic liquid compositions can comprise a phosphonium cation of the structure $PR^1R^2R^3R^4$, wherein $R^1$, $R^2$, $R^3$, and $R^4$ are independently H, halogen, substituted or unsubstituted $C_1$-$C_{20}$ alkyl, substituted or unsubstituted $C_1$-$C_8$ cycloalkyl, or wherein, as valence permits, two or more of $R^1$, $R^2$, $R^3$, and $R^4$, together with the atoms to which they are attached, form a 3-10 membered cyclic moiety. In some examples, $R^1$, $R^2$, $R^3$, and $R^4$ are independently H or substituted or unsubstituted $C_1$-$C_{20}$ alkyl. In some examples, $R^1$, $R^2$, $R^3$, and $R^4$ are independently H or unsubstituted $C_1$-$C_{14}$ alkyl. In some examples, $R^1$, $R^2$, $R^3$, and $R^4$ are independently unsubstituted $C_1$-$C_{14}$ alkyl. In some examples, the at least one phosphonium cation comprises $[(CH_2)_{13}CH_3P((CH_2)_5CH_3)_3]^+$.

In some examples, the ionic liquid catalyzing medium can comprise $[P_{66614}][Al_2Cl_7]$, where the notation "$P_{66614}$" indicates a trihexyltetradecylphosphonium group.

The catalyzing medium can be provided in an amount of from 1-100 mol % relative to the amount of acylating agent. In some examples, the catalyzing medium can be provided in an amount of from 1-50 mole %, from 1-10 mol %, from 1-5 mol %, or 5 mol % relative to the amount of acylating agent.

The aryl substrate can comprise a compound of formula I:

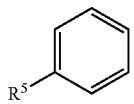

wherein $R^5$ is H, halogen, hydroxyl, substituted or unsubstituted $C_1$-$C_8$ alkyl, or substituted or unsubstituted $C_1$-$C_8$ cycloalkyl. In some examples, $R^5$ is substituted or unsubstituted $C_1$-$C_8$ alkyl. In some examples, $R^5$ is unsubstituted $C_1$-$C_8$ alkyl. In some examples, $R^5$ is unsubstituted $C_4$-$C_6$ alkyl. In some examples, $R^5$ is isobutyl.

In some examples, the acylating agent can comprise an acyl halide of formula II:

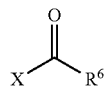

wherein X is a halogen; and $R^6$ is H, halogen, hydroxyl, substituted or unsubstituted $C_1$-$C_8$ alkyl, substituted or unsubstituted $C_1$-$C_8$ cycloalkyl, or substituted or unsubstituted aryl.

In some examples, X is chloride. In some examples, $R^6$ is substituted or unsubstituted $C_1$-$C_8$ alkyl. In some examples, $R^6$ is unsubstituted $C_1$-$C_8$ alkyl. In some examples, $R^6$ is unsubstituted $C_1$-$C_4$ alkyl. In some examples, $R^6$ is methyl.

In some examples, the acylating agent comprises an acyl an acid anhydride of formula III:

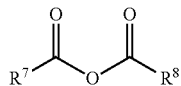

wherein $R^7$ and $R^8$ are independently H, halogen, hydroxyl, substituted or unsubstituted $C_1$-$C_8$ alkyl, substituted or unsubstituted $C_1$-$C_8$ cycloalkyl, substituted or unsubstituted aryl, or wherein, as valence permits, $R^7$ and $R^8$, together with the atoms to which they are attached, form a 4-10 membered cyclic moiety.

In some examples, $R^7$ and $R^8$ are independently H, halogen, hydroxyl, or substituted or unsubstituted $C_1$-$C_8$ alkyl. In some examples, $R^7$ and $R^8$ are independently substituted or unsubstituted $C_1$-$C_8$ alkyl. In some examples, $R^7$ and $R^8$ are independently unsubstituted $C_1$-$C_8$ alkyl. In some examples, $R^7$ and $R^8$ are independently unsubstituted $C_1$-$C_4$ alkyl. In some examples, the acylating agent comprises acetic anhydride.

In some examples, the substituted aryl substrate acylated in the para position is produced in a yield of 40% or more (e.g., 41% or more, 42% or more, 43% or more, 44% or more, 45% or more, 46% or more, 47% or more, 48% or more, 49% or more, 50% or more, 55% or more, 60% or more, 65% or more, 70% or more, 75% or more, 80% or more, 85% or more, 90% or more, or 95% or more).

In some examples, the method can be performed under an inert atmosphere, such as an argon (Ar) or nitrogen ($N_2$) atmosphere.

Combining the substituted aryl substrate with an acylating agent in the presence of a catalyzing medium can form a mixture. In some examples, the method can comprise heating the mixture at a temperature of 50° C. or more (e.g., 60° C. or more, 70° C. or more, 80° C. or more, 90° C. or more, 100° C. or more, 110° C. or more, 120° C. or more, or 130° C. or more). In some examples, the method can comprise heating the mixture at a temperature of 140° C. or less (e.g., 130° C. or less, 120° C. or less, 110° C. or less, 100° C. or less, 90° C. or less, 80° C. or less, 70° C. or less, or 60° C. or less). The temperature at which the mixture is heated can range from any of the minimum values described above to any of the maximum values described above. For example, the method can comprise heating the mixture at a temperature of from 50° C. to 140° C. (e.g., from 50° C. to 100° C., from 100° C. to 140° C., from 60° C. to 140° C., from 70° C. to 140° C., from 80° C. to 140° C., from 90° C. to 130° C., or from 100° C. to 120° C.).

In some examples, the mixture can be heated for 0.5 hours or more (e.g., 0.75 hours or more, 1 hour or more, 1.5 hours or more, 2 hours or more, 2.5 hours or more, 3 hours or more, 3.5 hours or more, 4 hours or more, 4.5 hours or more, 5 hours or more, or 5.5 hours or more). In some examples, the mixture can be heated for 6 hours or less (e.g., 5.5 hours or less, 5 hours or less, 4.5 hours or less, 4 hours or less, 3.5 hours or less, 3 hours or less, 2.5 hours or less, 2 hours or less, 1.5 hours or less, 1 hour or less, or 0.75 hours or less). The amount of time that the mixture is heated can range from any of the minimum values described above to any of the maximum values described above. For example, the mixture can be heated for from 0.5 hours to 6 hours (e.g., from 0.5 hours to 3 hours, from 3 hours to 6 hours, from 1 hour to 6 hours, from 2 hours to 6 hours, from 4 hours to 6 hours for from 4.5 hours to 5.5 hours).

In some examples, the methods can comprise heating the mixture at a temperature of from 100° C. to 120° C. for from 4 hours to 6 hours. In some examples, the methods can comprise heating the mixture at a temperature of 110° C. for 5 hours.

In some examples, the method can further comprise adding methanol or hexane to form a biphasic system.

In some examples, the method can be performed in the absence of HF. In some examples, wherein the method is used to produce an intermediate for the synthesis of ibuprofen. In some examples, the method produces 4-isobutylacetophenone. In some examples, the method produces 4-isobutylacetophenone with a selectivity of 90% or more (e.g., 91% or more, 92% or more, 93% or more, 94% or more, 95% or more, 96% or more, 97% or more, 98% or more, or 99% or more).

EXAMPLES

The following examples are set forth below to illustrate the methods and results according to the disclosed subject matter. These examples are not intended to be inclusive of all aspects of the subject matter disclosed herein, but rather to illustrate representative methods and results. These examples are not intended to exclude equivalents and variations of the present invention, which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures and other reaction ranges and conditions that can be used to optimize the product purity and yield obtained from the described process. Only reasonable and routine experimentation will be required to optimize such process conditions.

Anhydrous isobutylbenzene, and anhydrous acetic anhydride were purchased from Sigma-Aldrich (St. Louis, Mo.); while $AlCl_3$ (99% purity) and triethylammonium hydrochloride (98% purity) were purchased from Alfa Aesar (Ward Hill, Mass.). Dimethyl sulfoxide-$d_6$ (99.9% purity), used as NMR solvent, was purchased from Cambridge Isotope Laboratory, Inc (Andover, Mass.).

HF is still used in several conventional industrially important reactions, such as Ibuprofen intermediate synthesis, alkylation of benzene with olefin, etc. To overcome the limitations of hydrofluoric acid in the organic transformations, there is a need to develop environmentally safe, alternative acid catalysts. Ibuprofen has three major types of effect, which are all linked to its primary action, the inhibition of an enzyme known as arachidonate cyclooxygenase or COX; there are two types of the arachidonate cyclooxygenase, COX-1 and COX-2 (Hegazy G H and Ali H I. *Bio. Org. Med. Chem.* 2012, 20(3), 1259). Most routes to ibuprofen begin with isobutylbenzene and involve Friedel-Crafts acylation.

The product, 4-isobutylacetophenone, obtained from the acylation of isobutylbenzene is pharmaceutically important as it is largely used as an intermediate for the synthesis of ibuprofen and other pharmaceuticals (Scheme 1) (U.S. Pat. No. 3,385,886; Gore P H. in: Olah G A. (Ed.), Friedel—Crafts and Related Reactions, vol. III, Wiley/Interscience, New York, 1964, p. 64; Sheldon R A. *Chem. Ind.* 1992, 7, 903-906; Andy P. *J. Catal.* 2000, 192, 215-223). As shown in Scheme 1, the traditional catalysts used to synthesize 4-isobutylacetophenone from the acylation of isobutylbenzene are $AlCl_3$, HF, and zeolites, each of which suffers from various limitations.

In the acylation reaction of isobutylbenzene using HF to obtain 4-isobutylacetophenone, the HF is used in greater than stoichiometric amounts relative to isobutylbenzene (Sheldon R A. *Chem. Ind.* 1992, 7, 903-906). For commercial processes, $AlCl_3$ has also been used in the acylation of isobutylbenzene reaction, but the $AlCl_3$ was used in a more than stoichiometric amount relative to isobutylbenzene and in the presence of a solvent, and the reaction resulted in large amounts of waste and non-regenerable $AlCl_3$ (U.S. Pat. No. 3,385,886). Recently, solid acid catalyst like zeolites have been investigated in the reaction, but the yield obtained was low (<6%) (Andy P. *J. Catal.* 2000, 192, 215-222).

Scheme 1. Schematic representation of Ibuprofen synthesis.

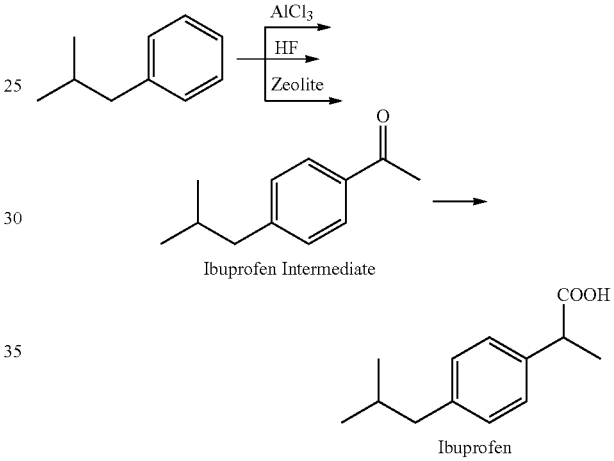

The two most popular ways to obtain ibuprofen from isobutylbenzene are the Boot process and the Hoechst process (Scheme 2). The Boot process is an older commercial process developed by the Boot Pure Drug Company (U.S. Pat. No. 3,385,886), and the Hoechst process is a newer process developed by the Hoechst Company. The Boot process involves six steps and results in the formation of by-products, while the Hoechst process involves three steps.

Scheme 2. Ibuprofen synthesis from isobutyl benzene via Boot process and Hoechst process.

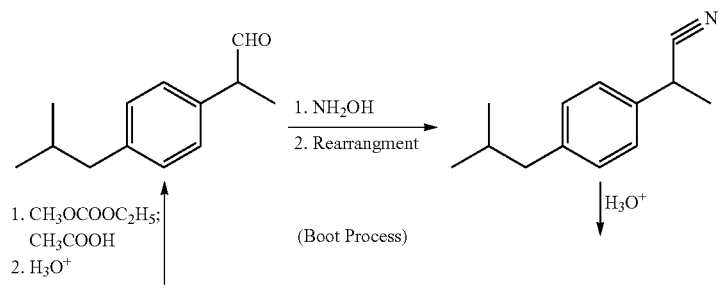

-continued

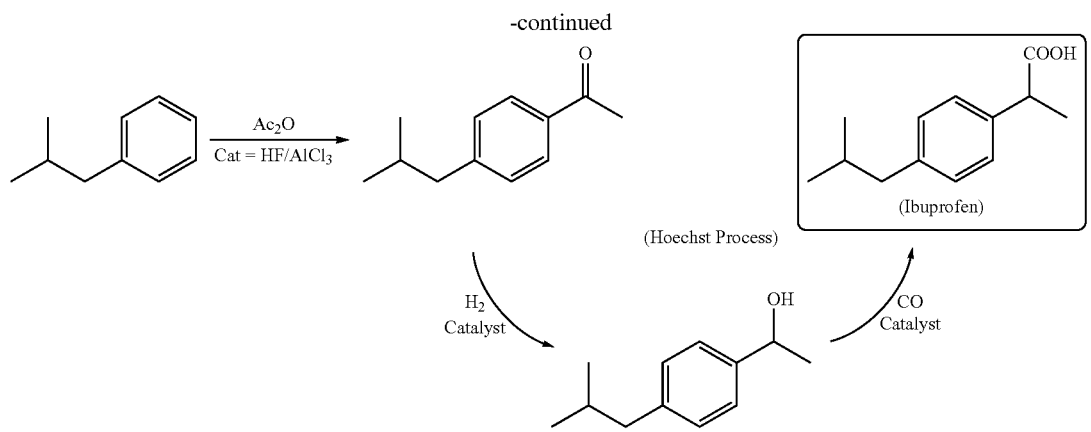

(Hoechst Process)

Discussed herein are methods for the acylation of isobutylbenzene using chloroaluminate ionic liquid. These methods can also be used to acylate other substituted aryl substrates. The chloroaluminate ionic liquid disclosed herein can be used for the acylation of isobutylbenzene and other substituted aryl substrates, an industrially important process for the replacement of HF/AlCl$_3$. The examples of chloroaluminate ionic liquids such as AL-2100 (prepared following the procedure from WO 2014/178075), triethylammonium chloroaluminate ionic liquid, N-methyl-2-pyrrolidone (NMP)-AlCl$_3$ adduct based ionic liquid, and trihexyl(tetradecyl)phosphonium chloroaluminate ionic liquid etc.

The chloroaluminate ionic liquid can, for example, be prepared following the procedure from WO 2014/178075. Ionic liquids are typically non-volatile liquids and the acidic ionic liquids used herein were used to replace the commercially used toxic and volatile HF in the acid catalyzed Ibuprofen intermediate synthesis.

Currently utilized technologies for acylation of isobutylbenzene reaction suffer from drawbacks such as the safety issues and volatility of HF, the requirement of additional processing for de-acidification of AlCl$_3$, and the inefficiency of solid acid zeolite catalyst. The ionic liquids address almost all of the drawbacks of existing catalysts used in the acylation of isobutylbenzene. Properties of chloroaluminate ionic liquids such as (a) tunable acidity through varying the ratios of metals results in an increased efficiency and (b) low vapor pressure can improve the safety of these ionic liquids as compared to the use of highly toxic and volatile HF. The chloroaluminate ionic liquid herein investigated for the acylation of isobutylbenzene, an industrially important process, was [HN$_{222}$][Al$_2$Cl$_7$]. The [HN$_{222}$][Al$_2$Cl$_7$] was prepared according to the process described in U.S. Pat. No. 5,824,832.

In an Ar-filled glove bag, a 5 mL borosilicate glass screw-top vial equipped with a Teflon coated magnetic stir bar was loaded with 0.4 mmol of [HN$_{222}$][Al$_2$Cl$_7$] (5 mol % with respect to the amount of acetic anhydride) followed by addition of 32 mmol of isobutylbenzene and 8 mmol of acetic anhydride. After addition of the reactants, the mixture was observed to form a colorless liquid with small black spots dispersed therein (FIG. 1). The vial was capped using a rubber septum, and sealed with Parafilm. The vial was then removed from the glove bag and the reaction mixture was heated in a temperature controlled oil bath with magnetic stirring at 110° C. for 5 h (Scheme 3). After 5 h the vial was removed from oil bath and left to cool on the bench top, giving a liquid with a faint orange solid precipitate (FIG. 1).

Figure 2:
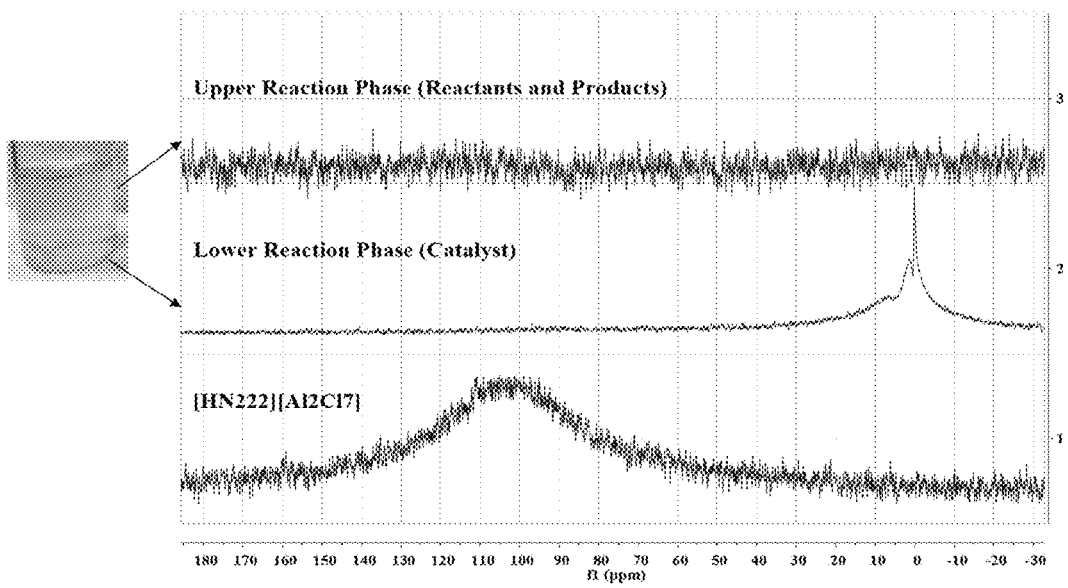
FIG. 2 shows the $^{27}Al$ NMR of layers separated from the acylation of isobutylbenzene reaction: Upper layer (top spectrum) and Lower layer (middle spectrum), compared with solventless catalyst (bottom spectrum) (27° C., neat, DSMO-$d_6$ lock).

Methanol (1 mL) was added to the reaction mixture to form a biphasic liquid system with a faint orange upper layer and a colorless lower layer (FIG. 1). $^{27}$Al NMR analysis of both layers confirms that the Al is present only in the lower layer while the reactants and products are present only in the upper layer (FIG. 2). This indicates that after reaction, the product as well as the catalyzing medium can be separated by decantation.

Scheme 3. Acylation of isobutylbenzene reaction using chloroaluminate ILs.

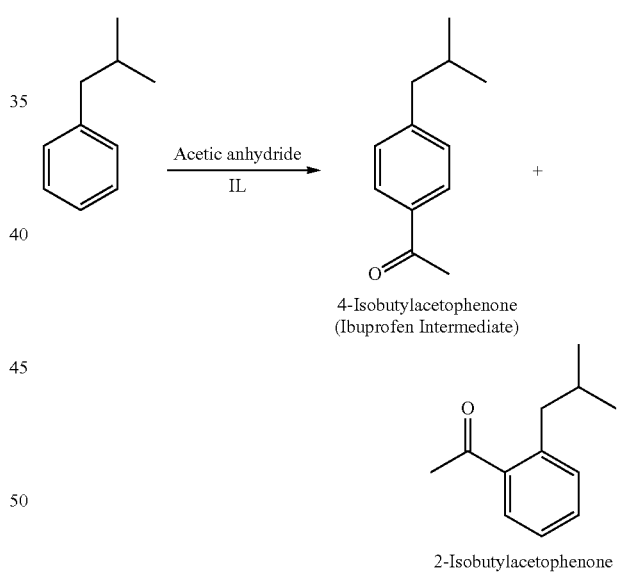

A small aliquot mixture from the upper layer of the reaction mixture was withdrawn and further diluted with methanol. A 47% conversion with 97% 4-isobutyl acetophenone product selectivity was observed in analysis with gas chromatography coupled to mass spectrometer (GC-MS, HP 6890 GC series connected to a Water Micromass AUTOSPEC-ULTIMA™ NT Mass spectrometer, Waters, Milford, Mass.). Conditions of the run: starting temperature of 30° C. and a hold time of 3 min, a ramp rate of 5° C. min$^{-1}$, and a final temperature of 200° C., with a hold time of 20 min; Zebron ZB-5MS column (30 m length, 250 μm internal diameter, column coating thickness of 25 μm), EI source temperature 220° C.

To investigate the effect of the catalyst quantity in the acylation of isobutylbenzene reaction, different amounts of the $[HN_{222}][Al_2Cl_7]$ catalyst were used, from 5 to 40 mol % with respect to the amount of acetic anhydride used. The 5% mol the $[HN_{222}][Al_2Cl_7]$ catalyst reaction is described above.

Figure 3:
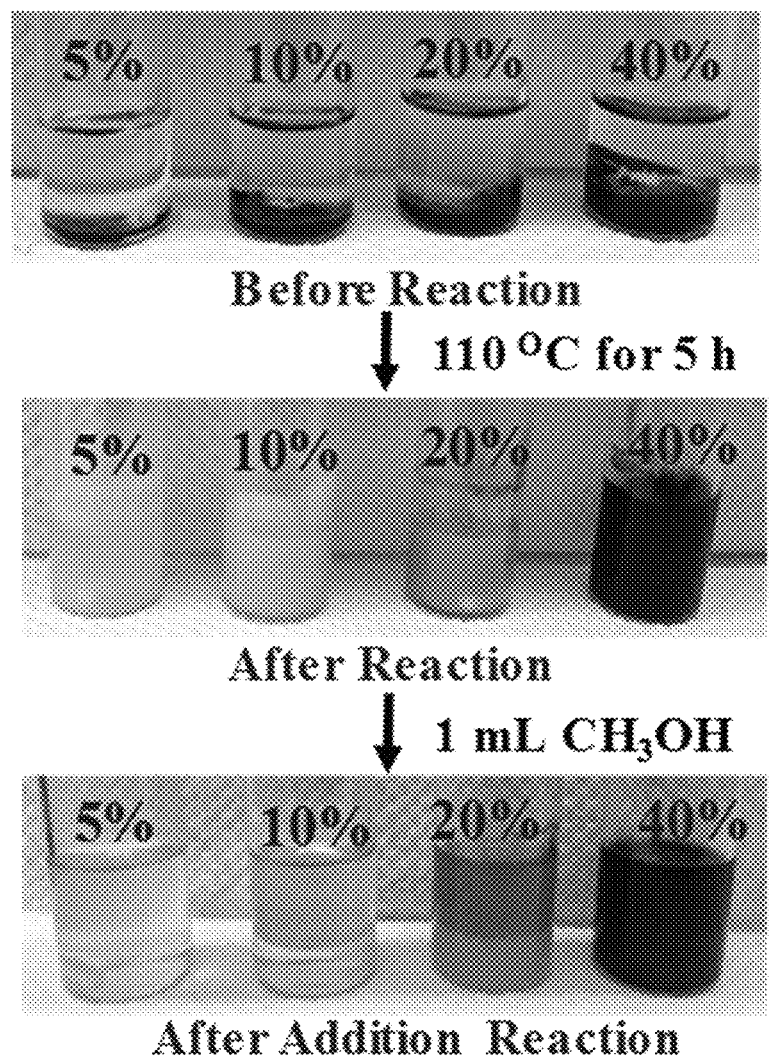
FIG. 3 shows photographs illustrating the physical observations of the reaction mixture during the acylation of isobutylbenzene using different amounts of the chloroaluminate ionic liquid.

For the 10 mol % of the $[HN_{222}][Al_2Cl_7]$ catalyst, in an Ar-filled glove bag, a 5 mL borosilicate glass screw-top vial equipped with a Teflon coated magnetic stir bar was loaded with 0.80 mmol of $[HN_{222}][Al_2Cl_7]$ (10 mol % with respect to the amount of acetic anhydride used) followed by addition of 32 mmol of isobutylbenzene and further 8 mmol of acetic anhydride. After addition of the reactants, a black color was observed at the bottom of the colorless liquid (FIG. 3). The vial was capped using a rubber septum, and sealed with Parafilm. The vial was then removed from the glove bag and the reaction mixture was heated in a temperature controlled oil bath with magnetic stirring at 110° C. for 5 h. After 5 h the vial was removed from oil bath and left to cool on the bench top, giving a liquid with a faint orange solid precipitate (FIG. 3). Further, 1 mL methanol was added in the reaction mixture to form a biphasic liquid system which has a faint orange upper layer and a colorless lower layer (FIG. 3). A small aliquot from the upper layer was withdrawn and further diluted with methanol and monitored by using GC-MS. From GC-MS, 89% conversion with 96% 4-isobutyl acetophenone product selectivity was obtained.

For the 20 mol % of the $[HN_{222}][Al_2Cl_7]$ catalyst, in an Ar-filled glove bag, a 5 mL borosilicate glass screw-top vial equipped with a Teflon coated magnetic stir bar was loaded with 1.6 mmol of $[HN_{222}][Al_2Cl_7]$ followed by addition of 32 mmol of isobutylbenzene and further 8 mmol of acetic anhydride. After addition of the reactants, black color appeared at the bottom of the colorless liquid (FIG. 3). The vial was capped using a rubber septum, and sealed with Parafilm. The vial was then removed from the glove bag and the reaction mixture was heated in a temperature controlled oil bath with magnetic stirring at 110° C. for 5 h. After 5 h the vial was removed from oil bath and left to cool on the bench top, giving a liquid with a faint orange solid precipitate (FIG. 3). Further, 1 mL methanol was added in the reaction mixture, then a biphasic liquid system with a faint orange upper layer and a colorless lower layer with crystals dispersed therein was observed (FIG. 3). A small aliquot from the upper layer was withdrawn and further diluted with methanol and monitored by GC-MS. From GC-MS, 97% conversion with 94% 4-isobutyl acetophenone product selectivity was obtained. The crystals were handpicked from the lower layer of the reaction mixture and were analyzed on the SCXRD machine. The crystal was indexed and matched with reported structure of $[HN_{222}Cl]$ (Churakova A V and Howard J A K. *Acta Crystallogr., Sect. C: Cryst. Struct. Commun.* 2004, 60, 557-558).

For the 30 mol % of the $[HN_{222}][Al_2Cl_7]$ catalyst, in an Ar-filled glove bag, a 5 mL borosilicate glass screw-top vial equipped with a Teflon coated magnetic stir bar was loaded with 2.4 mmol of $[HN_{222}][Al_2Cl_7]$ followed by addition of 32 mmol of isobutylbenzene and further 8 mmol of acetic anhydride. After addition of the reactants, black color appeared at the bottom of the colorless liquid (FIG. 3). The vial was capped using a rubber septum and sealed with Parafilm. The vial was then removed from the glove bag and the reaction mixture was heated in a temperature controlled oil bath with magnetic stirring at 110° C. for 5 h. After 5 h the vial was removed from oil bath and left to cool on the bench top, giving a black liquid and a black solid precipitate (FIG. 3). Further, 1 mL methanol was added in the reaction mixture then a biphasic liquid system with a dark black upper layer and a light black lower layer was observed (FIG. 3). A small aliquot from the upper layer was withdrawn and further diluted with methanol and monitored by using GC-MS. From GC-MS, 99% conversion with 93% 4-isobutyl acetophenone product selectivity was obtained.

For the 40 mol % of the $[HN_{222}][Al_2Cl_7]$ catalyst, in an Ar-filled glove bag, a 5 mL borosilicate glass screw-top vial equipped with a Teflon coated magnetic stir bar was loaded with 3.2 mmol of $[HN_{222}][Al_2Cl_7]$ followed by addition of 32 mmol of isobutylbenzene and further 8 mmol of acetic anhydride. After addition, black color appeared at the bottom of the colorless liquid (FIG. 3). The vial was capped using a rubber septum and sealed with parafilm. The vial was then removed from the glove bag and the reaction mixture was heated in a temperature controlled oil bath with magnetic stirring at 110° C. for 5 h. After 5 h the vial was removed from oil bath and left to cool on the bench top, giving a black liquid with a black solid precipitate (FIG. 3). Further, 1 mL methanol was added in the reaction mixture then a biphasic liquid system containing a dark black upper layer and a light black lower layer was observed (FIG. 3). A small aliquot from the upper layer was withdrawn and further diluted with methanol and monitored by using GC-MS. From GC-MS, 99% conversion with 93% 4-isobutyl acetophenone product selectivity was obtained.

Figure 4:
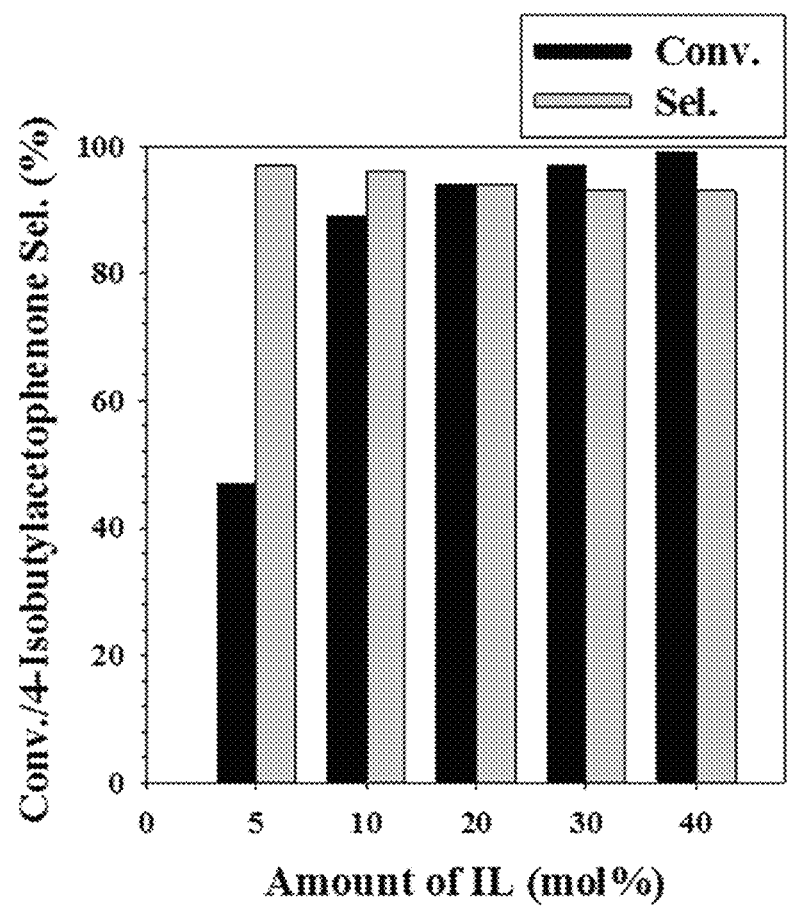
FIG. 4 shows the comparative catalytic activity data for the acylation of isobutylbenzene using different amount of the chloroaluminate ionic liquid.

As can be seen in FIG. 3, there was a difference in physical appearance with increasing the amount of $[HN_{222}][Al_2Cl_7]$ ionic liquid catalyst in the reaction mixture. FIG. 4 summarized the GC-MS results obtained from the aliquot taken from each of the upper layers. As can be seen in FIG. 4, as the amount of $[HN_{222}][Al_2Cl_7]$ ionic liquid catalyst increases from 5 to 40 mol %, the activity increases from 47 to 99%, but with a slight decrease in product selectivity.

The effect of the amount of isobutylbenzene in the acylation of isobutylbenzene was investigated by using from 2 to 8 equivalents of isobutylbenzene with respect to acetic anhydride in the reaction (using a 5 mol % of $[HN_{222}][Al_2Cl_7]$ for each case).

For the 2 equivalents of isobutylbenzene with respect to acetic anhydride, in an Ar-filled glove bag, a 5 mL borosilicate glass screw-top vial equipped with a Teflon coated magnetic stir bar was loaded with 0.4 mmol of $[HN_{222}][Al_2Cl_7]$ followed by addition of 16 mmol of isobutylbenzene and further 8 mmol of acetic anhydride. After addition of the reactants, black color appeared at the bottom of the colorless liquid. The vial was capped using a rubber septum, and sealed with Parafilm. The vial was then removed from the glove bag and the reaction mixture was heated in a temperature controlled oil bath with magnetic stirring at 110° C. for 5 h. After 5 h the vial was removed from oil bath and left to cool on the bench top, giving a faint orange precipitate solid. Further, 1 mL methanol was added in the reaction mixture then a biphasic liquid system containing a faint orange upper layer and a colorless lower layer was observed. A small aliquot from the upper layer was withdrawn and further diluted with methanol and monitored by using GC-MS. From GC-MS, 53% conversion with 96% 4-isobutyl acetophenone product selectivity was obtained.

For the 4 equivalents of isobutylbenzene with respect to acetic anhydride, in an Ar-filled glove bag, a 5 mL borosilicate glass screw-top vial equipped with a Teflon coated magnetic stir bar was loaded with 0.4 mmol of $[HN_{222}][Al_2Cl_7]$ (5 mol % with respect to the amount of acetic anhydride) followed by addition of 32 mmol of isobutylbenzene and 8 mmol of acetic anhydride, as described above.

For the 8 equivalents of isobutylbenzene with respect to acetic anhydride, in an Ar-filled glove bag, a 5 mL borosilicate glass screw-top vial equipped with a Teflon coated magnetic stir bar was loaded with 0.4 mmol of [HN$_{222}$][Al$_2$Cl$_7$] followed by addition of 64 mmol of isobutylbenzene and further 8 mmol of acetic anhydride. After addition of the reactants, black color appeared at the bottom of the colorless liquid. The vial was capped using a rubber septum and sealed with Parafilm. The vial was then removed from the glove bag and the reaction mixture was heated in a temperature controlled oil bath with magnetic stirring at 110° C. for 5 h. After 5 h the vial was removed from oil bath and left to cool on the bench top, giving a faint orange precipitate solid as well as faint orange liquid. Further, 1 mL methanol was added in the reaction mixture then a biphasic liquid system containing a faint orange upper layer and a colorless lower layer was observed. A small aliquot from the upper layer was withdrawn and further diluted with methanol and monitored by using GC-MS. From GC-MS, 46% conversion with 96% 4-isobutyl acetophenone product selectivity was obtained.

Figure 5:
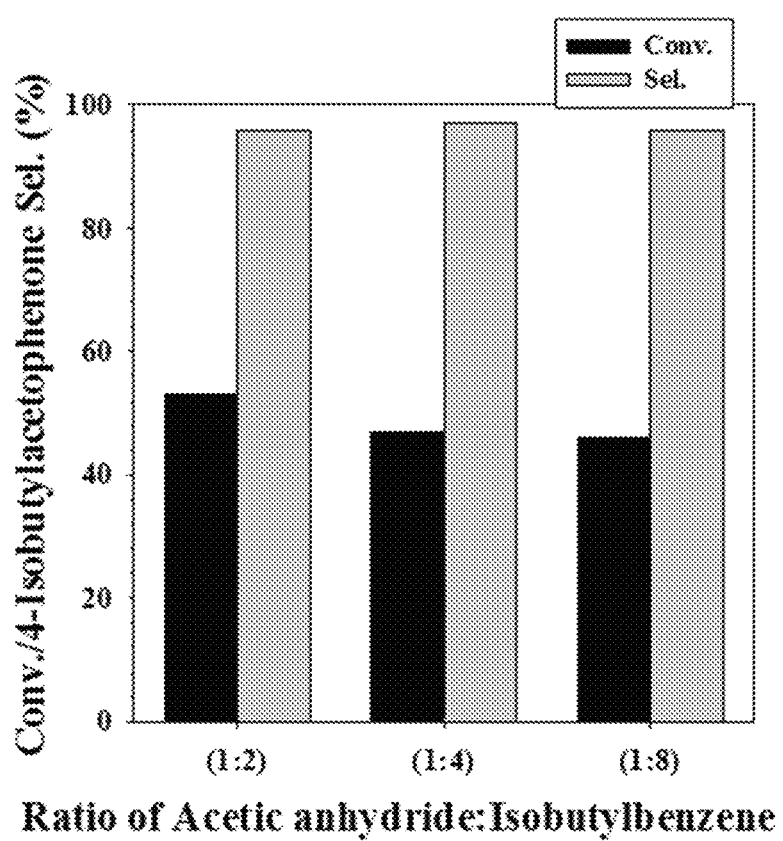
FIG. 5 shows the comparative catalytic activity data for the acylation of isobutylbenzene with different amounts of isobutyl benzene.

For the reactions with different amounts of acetic anhydride:isobutylbenzene, there were changes in the physical appearance of the reaction mixture as the ratio of acetic anhydride:isobutylbenzene increased. For example, the amount of the top liquid layer in the biphasic system increased as the amount of isobutylbenzene in the reaction increased. The GC-MS results for the reactions run with different ratios of acetic anhydride:isobutylbenzene are summarized in the FIG. 5. As can be seen from FIG. 5, changes the ratio of acetic anhydride:isobutylbenzene had no significant effect on the catalytic activity.

In addition to [HN$_{222}$][Al$_2$Cl$_7$], another ionic liquid referred to as AL-2100, was investigated as a catalyst for the acylation of isobutylbenzene. The ionic liquid AL-2100 was prepared according to the procedure described in WO 2014/178075. Specifically, AL-2100 was prepared in two steps. In first step, a trimethylamine (N$_{222}$)—AlCl$_3$ adduct was prepared by reacting N$_{222}$ and AlCl$_3$ in a 1:3 molar ratio in ethyl acetate as solvent. In the second step, the N$_{222}$—AlCl$_3$ adduct was further reacted with 2 equivalents of AlCl$_3$ under neat conditions at room temperature to obtain liquid AL-2100 ([(N$_{222}$)$_3$—Al][(AlCl$_3$)$_6$Cl$_3$]).

For the acylation of isobutylbenzene, in an Ar-filled glove bag, a 5 mL borosilicate glass screw-top vial equipped with a Teflon coated magnetic stir bar was loaded with 0.80 mmol of AL-2100 followed by addition of 32 mmol of isobutylbenzene and further 8 mmol of acetic anhydride. After addition of the reactants, black color appeared at the bottom of the colorless liquid. The vial was capped using a rubber septum, and sealed with Parafilm. The vial was then removed from the glove bag and the reaction mixture was heated in a temperature controlled oil bath with magnetic stirring at 110° C. for 5 h. After 5 h the vial was removed from oil bath and left to cool on the bench top, giving a liquid with a faint orange solid precipitate. Further, 1 mL methanol was added in the reaction mixture, then a biphasic liquid system containing a faint orange upper layer and a colorless lower layer was observed. A small aliquot from the upper layer was withdrawn and further diluted with methanol and monitored by using GC-MS. From GC-MS, 95% conversion with 96% 4-isobutyl acetophenone product selectivity was obtained.

In addition, an N-methyl pyrrolidone (NMP)-AlCl$_3$ adduct based ionic liquid (at 0.6 molar ratio of AlCl$_3$) was prepared and investigated as a catalyst for the acylation of isobutylbenzene. The NMP-AlCl$_3$ adduct was prepared by addition of N-methyl pyrrolidone (NMP) and AlCl$_3$ with a 1:1.5 molar ratio under Ar atmosphere at room temperature. The reaction mixture was heated at 100° C. for 4 h, then cooled to room temperature to obtain a viscous grey black liquid. The NMP-AlCl$_3$ adduct based IL can comprise [AlCl$_2$(NMP)$_2$][Al$_2$Cl$_7$].

For the acylation of isobutylbenzene, in an Ar-filled glove bag, a 5 mL borosilicate glass screw-top vial equipped with a Teflon coated magnetic stir bar was loaded with 0.80 mmol of NMP-AlCl$_3$ adduct based ionic liquid followed by addition of 32 mmol of isobutylbenzene and further 8 mmol of acetic anhydride. After addition of the reactants, black color appeared at the bottom of the colorless liquid. The vial was capped using a rubber septum, and sealed with Parafilm. The vial was then removed from the glove bag and the reaction mixture was heated in a temperature controlled oil bath with magnetic stirring at 110° C. for 5 h. After 5 h the vial was removed from oil bath and left to cool on the bench top, giving a liquid with a faint orange solid precipitate. Further, 1 mL methanol was added in the reaction mixture, then a biphasic liquid system containing a faint orange upper layer and a colorless lower layer was observed. A small aliquot from the upper layer was withdrawn and further diluted with methanol and monitored by using GC-MS. From GC-MS, 99% conversion with 96% 4-isobutyl acetophenone product selectivity was obtained.

In addition, a [P$_{66614}$][Al$_2$Cl$_7$] ionic liquid (where the notation "P$_{66614}$" indicates a trihexyltetradecylphosphonium group) was prepared and investigated as a catalyst for the acylation of isobutylbenzene. The [P$_{66614}$][Al$_2$Cl$_7$] ionic liquid was prepared by addition of [P$_{66614}$][Cl] and AlCl$_3$ with a 1:2 molar ratio under Ar atmosphere at room temperature. The reaction mixture was heated at 80° C. for 4 h and then cooled to room temperature to obtain viscous dark brown liquid.

For the acylation of isobutylbenzene, in an Ar-filled glove bag, a 5 mL borosilicate glass screw-top vial equipped with a Teflon coated magnetic stir bar was loaded with 0.40 mmol of [P$_{66614}$][Al$_2$Cl$_7$] followed by addition of 32 mmol of isobutylbenzene and further 8 mmol of acetic anhydride. After addition of the reactants, black color appeared at the bottom of the colorless liquid. The vial was capped using a rubber septum, and sealed with Parafilm. The vial was then removed from the glove bag and the reaction mixture was heated in a temperature controlled oil bath with magnetic stirring at 110° C. for 5 h. After 5 h the vial was removed from oil bath and left to cool on the bench top, giving a liquid with a faint orange solid precipitate. Further, 1 mL methanol was added in the reaction mixture, then a biphasic liquid system containing a faint orange upper layer and a colorless lower layer was observed. A small aliquot from the upper layer was withdrawn and further diluted with methanol and monitored by using GC-MS.

A process for the preparation of 4-isobutylbenzene from the acylation of isobutylbenzene using ionic liquids such as triethylammonium chloroaluminate, AL-2100, NMP-AlCl$_3$ adduct based ionic liquid have been discussed herein. The product 4-isobutylacetophenone from the reaction is largely used as an intermediate for the synthesis of Ibuprofen. The process discussed herein avoids the use of hydrofluoric acid (HF), an extremely toxic chemical typically used for this process in greater than stoichiometric amounts relative to isobutylbenzene. The preliminary data show that when 5 to 40 mol % of the ionic liquids are used as the catalyst, then 47 to 100% conversions with 93 to 97% 4-isobutylacetophenone selectivity were observed. The product can be isolated by addition of methanol to the reaction mixture to form a biphasic system.

The methods and compositions of the appended claims are not limited in scope by the specific methods and compositions described herein, which are intended as illustrations of a few aspects of the claims and any methods and compositions that are functionally equivalent are within the scope of this disclosure. Various modifications of the methods and compositions in addition to those shown and described herein are intended to fall within the scope of the appended claims. Further, while only certain representative methods, compositions, and aspects of these methods and compositions are specifically described, other methods and compositions and combinations of various features of the methods and compositions are intended to fall within the scope of the appended claims, even if not specifically recited. Thus a combination of steps, elements, components, or constituents can be explicitly mentioned herein; however, all other combinations of steps, elements, components, and constituents are included, even though not explicitly stated.

What is claimed is:

1. A method of acylating an aryl substrate, comprising: combining a substituted aryl substrate with an acylating agent in the presence of a catalyzing medium, thereby acylating the substituted aryl substrate in the para position;
wherein the catalyzing medium is an ionic liquid comprising at least one cation and at least one metal halide anion, wherein the ionic liquid is a salt of the at least one cation and the at least one metal halide anion with a melting point of 150° C. or less, and wherein the at least one metal halide anion comprises $[Al_2Cl_7]^-$;
wherein the aryl substrate comprises a compound of formula I:

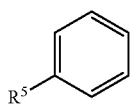

I wherein $R^5$ is H, halogen, hydroxyl, substituted or unsubstituted $C_1$-$C_8$ alkyl, or substituted or unsubstituted $C_1$-$C_8$ cycloalkyl;
wherein the acylating agent comprises an acyl halide of formula II or an acid anhydride of formula III:

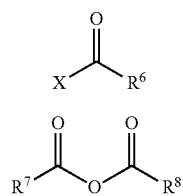

II

III wherein
X is a halogen;
$R^6$ is H, halogen, hydroxyl, substituted or unsubstituted $C_1$-$C_8$ alkyl, substituted or unsubstituted $C_1$-$C_8$ cycloalkyl, or substituted or unsubstituted aryl; and $R^7$ and $R^8$ are independently H, halogen, hydroxyl, substituted or unsubstituted $C_1$-$C_8$ alkyl, substituted or unsubstituted $C_1$-$C_8$ cycloalkyl, substituted or unsubstituted aryl, or wherein, as valence permits, $R^7$ and $R^8$, together with the atoms to which they are attached, form a 4-10 membered cyclic moiety.

2. The method of claim 1, wherein the at least one cation is an ammonium, an imidazolium, a pyridinium, a phosphonium, a sulphonium, or a combination thereof.

3. The method of claim 1, wherein the at least one cation comprises an ammonium cation of the structure $NR^1R^2R^3R^4$, wherein $R^1$, $R^2$, $R^3$, and $R^4$ are independently H, halogen, substituted or unsubstituted $C_1$-$C_{14}$ alkyl, substituted or unsubstituted $C_1$-$C_8$ cycloalkyl, or wherein, as valence permits, two or more of $R^1$, $R^2$, $R^3$, and $R^4$, together with the atoms to which they are attached, form a 3-10 membered cyclic moiety.

4. The method of claim 3, wherein $R^1$, $R^2$, $R^3$, and $R^4$ are independently H or substituted or unsubstituted $C_1$-$C_{14}$ alkyl.

5. The method of claim 1, wherein the at least one cation comprises a phosphonium cation of the structure $PR^1R^2R_3R^4$, wherein $R^1$, $R^2$, $R^3$, and $R^4$ are independently H, halogen, substituted or unsubstituted $C_1$-$C_{20}$ alkyl, substituted or unsubstituted $C_1$-$C_8$ cycloalkyl, or wherein, as valence permits, two or more of $R^1$, $R^2$, $R^3$, and $R^4$, together with the atoms to which they are attached, form a 3-10 membered cyclic moiety.

6. The method of claim 5, wherein $R^1$, $R^2$, $R^3$, and $R^4$ are independently H or substituted or unsubstituted $C_1$-$C_{20}$ alkyl.

7. The method of claim 1, wherein the at least one cation comprises $[AlCl_2(n\text{-methyl-2-pyrrolidone})_2]^+$, $[(CH_2)_{13}CH_3P((CH_2)_5CH_3)_3]^+$, $[HN(C_2H_5)_3]^+$, or a combination thereof.

8. The method of claim 1, wherein the catalyzing medium is an ionic liquid comprising $[HN(C_2H_5)_3][Al_2Cl_7]$, $[(CH_2)_{13}CH_3P((CH_2)_5CH_3)_3][Al_2Cl_7]$, $[AlCl_2(n\text{-methyl-2-pyrrolidone})_2][Al_2Cl_7]$, or a combination thereof.

9. The method of claim 1, wherein $R^5$ is substituted or unsubstituted $C_1$-$C_8$ alkyl.

10. The method of claim 1, wherein the acylating agent comprises an acyl an acid anhydride of formula III:

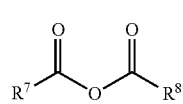

III wherein $R^7$ and $R^8$ are independently H, halogen, hydroxyl, substituted or unsubstituted $C_1$-$C_8$ alkyl, substituted or unsubstituted $C_1$-$C_8$ cycloalkyl, substituted or unsubstituted aryl, or wherein, as valence permits, $R^7$ and $R^8$, together with the atoms to which they are attached, form a 4-10 membered cyclic moiety.

11. The method of claim 10, wherein $R^7$ and $R^8$ are independently H, halogen, hydroxyl, or substituted or unsubstituted $C_1$-$C_8$ alkyl.

12. The method of claim 1, wherein the acylating agent comprises acetic anhydride.

13. The method of claim 1, wherein the catalyzing medium is provided in an amount of from 1-50 mol % relative to the amount of acylating agent.

14. The method of claim 1, wherein the method is performed in the absence of HF.

15. The method of claim 1, wherein the method produces 4-isobutylacetophenone.

16. The method of claim 1, wherein the substituted aryl substrate acylated in the para position is produced in a yield of 40% or more.

17. The method of claim 1, wherein the method is used to produce an intermediate for the synthesis of ibuprofen.

* * * * *